United States Patent [19]

Petrovich

[11] 4,378,351

[45] Mar. 29, 1983

[54] METHODS OF TREATING BACTERIAL, VIRAL OR PARASITIC DISEASES

[76] Inventor: Vojislav Petrovich, 1935 W. Schiller St., Chicago, Ill. 60622

[21] Appl. No.: 425,487

[22] Filed: Sep. 28, 1982

Related U.S. Application Data

[63] Continuation-in-part of Ser. No. 187,584, Sep. 15, 1980, abandoned, and a continuation-in-part of Ser. No. 187,585, Sep. 15, 1980, abandoned, and a continuation-in-part of Ser. No. 196,862, Sep. 14, 1980, abandoned, and a continuation-in-part of Ser. No. 233,036, Feb. 9, 1981, abandoned, and a continuation-in-part of Ser. No. 233,037, Feb. 9, 1981, abandoned, and a continuation-in-part of Ser. No. 287,428, Jul. 27, 1981, abandoned, and a continuation-in-part of Ser. No. 288,302, Jul. 30, 1981, abandoned, and a continuation-in-part of Ser. No. 288,304, Jul. 30, 1981, abandoned, and a continuation-in-part of Ser. No. 294,849, Aug. 21, 1981, abandoned, and a continuation-in-part of Ser. No. 294,850, Aug. 21, 1981, abandoned, and a continuation-in-part of Ser. No. 298,178, Aug. 31, 1981, abandoned, and a continuation-in-part of Ser. No. 400,590, Jul. 22, 1982, abandoned, and a continuation-in-part of Ser. No. 400,591, Jul. 22, 1982, abandoned, and a continuation-in-part of Ser. No. 400,592, Jul. 22, 1982, abandoned.

[51] Int. Cl.$^3$ .................... A61K 33/04; A61K 31/19; A61K 31/205

[52] U.S. Cl. .................... 424/164; 424/317; 424/319

[58] Field of Search ................ 424/164, 317, 319

[56] References Cited

U.S. PATENT DOCUMENTS

| | | |
|---|---|---|
| 2,917,429 | 12/1959 | Scott . |
| 3,167,471 | 1/1965 | Kovacs . |
| 3,846,459 | 11/1974 | Stapfer . |
| 3,976,781 | 8/1976 | Kalopissis . |
| 4,107,330 | 8/1978 | Sheffner . |
| 4,148,885 | 4/1979 | Renonx . |
| 4,151,301 | 4/1979 | Kalopissis . |

FOREIGN PATENT DOCUMENTS 2917790 11/1979 Fed. Rep. of Germany .

*Primary Examiner*—Anna P. Fagelson

[57] ABSTRACT

The invention relates to a therapeutic mixture for treating bacterial and viral infections and exterminating parasites in human and animal host; comprises a therapeutically effective mixture consisting of cysteine sodium salt, and disodium sulfite, which in conjunction perform after injection a permanent reducing action liberating charged hydrogen, and charged aminothiopropionic acid radical, which are biologically active neutralizing and transforming bacteria and viruses, and kill the parasites.

3 Claims, No Drawings

METHODS OF TREATING BACTERIAL, VIRAL OR PARASITIC DISEASES

This application is a continuation in part of the applications:

Ser. No. 187,584, filed Sept. 15, 1980, Ser. No. 187,585, filed Sept. 15, 1980, Ser. No. 196,862, filed Sept. 14, 1980, Ser. No. 233,036 filed Feb. 9, 1981 Ser. No. 233,037, filed Feb. 9, 1981, Ser. No. 287,428, filed July 27, 1981, Ser. No. 288,302, filed July 30, 1981, Ser. No. 288,304, filed July 30, 1981, Ser. No. 294,849, filed Aug. 21, 1981, Ser. No. 294,850, filed Aug. 21, 1981, Ser. No. 298,178, filed Aug. 31, 1981 Ser. No. 400,590, filed July 22, 1982 Ser. No. 400,591, filed July 22, 1982, Ser. No. 400,592, filed July 22, 1982, which are abandoned.

This invention relates to a therapeutic action of reducing media for controlling bacterial and viral infection and parasitic infestation in human and animal host, by applying a therapeutic mixture consisting of Cysteine which is aminomercaptopropionic acid, and disodium sulfite. Said aminomercaptopropionic sodium salt in conjunction with reducing disodium sulfite perform after injection a permanent reducing action liberating charged hydrogen, and charged aminothiopropionic radical which are biologically active which is manifested by neutralizing, or transforming the bacteria and viruses to nonagressive macromolecules, while killing parasites.

The mechanism of action of cysteine the aminomercaptopropionic sodium salt in conjunction with disodium sulfite unfolds a reducing process in a reducing media, which consequently contributes to the developement of nascent and biologically active charged hydrogen, as well as the development of nascent charged aminothiopropionic radical. The supposedly antibacterial and antiviral action is accomplished by the integration of charged hydrogen and charged aminothiopropionic radical from reduced aminomercaptopropionic sodium salt, which complete the bacterial and viral nucleoproteides and thus neutralize their activity, while charged aminothiopropionic radical which being unstable, when unite to diaminodithiopropionic acid in the presence of parasites, said diaminopropionic disulfide is poisonous to parasites and thus kills them.

The regenerative reversible process in the formation of aminothiopropionic and aminomercaptopropionic acid to release the active charged hydrogen develops by inherent oxidizing process and the reducing action of disodium sulfite. The reverse process is manifested in permanently reducing charged aminothiopropionic acid to aminomercaptopropionic acid as long as it is of disposable hydrogen from sulfite reducing action developed by hydrolysis. Each oxidation and reduction is sustained in reversible conditions, which is very important timely and biologically.

Reversible oxidation and reduction of aminomercaptopropionic acid makes feasible that the combination of said compound with mild reducing agent such as disodium sulfite, partake in the formation of biologically active hydrogen, i.e., charged hydrogen and charged aminothiopropionic radical. Combining charged hydrogen and charged aminothiopropionic radical follows de-oxidation and neutralization of bacteria and viruses unsaturated macromolecules, while the parasites under such conditions are killed. Thus, the nascent charged hydrogen, and nascent charged aminothiopropionic radical by their reactivity promote the antibacterial and antiviral action, as well as provoke the killing of parasites, which is the essence of this invention.

The charged hydrogen and the charged aminothiopropionic radical are capable to bind unsaturated compounds on which behavior is based antibacterial and antiviral action of this invention. For, macromolecules undoubtedly have no homogeneous charge distribution, which should provide potential sites for trapping displaced electrons or binding holes in addition to those sites associated with lattice imperfection.

The advantage of disclosed pharmacologically active reducing media with charged hydrogen radical, charged aminothiopropionic radical, resides in nontoxic quality of disclosed process. No side effects can be expected by application of simple aminomercaptopropionic sodium salt, aided by disodium sulfite with reducing capabilities by evolving disposable charged hydrogen. The aminothiopropionic radical is of short duration, because emitting charged hydrogen. Therefore, no toxic action may be incurred anyhow. The aminomercaptopropionic acid is to some extent toxic, if used with disodium sulfite of which the dose may be several times bigger because of acting redoxy process. The said aminothiopropionic acid being unstable in neutral and weakly alkaline media as is the blood serum oxidizes to disulfide diacid by emitting hydrogen. The presence of disodium sulfite prevent the formation of disulfide, as well as the presence of parasites, which is always present in said process but is of short duration. The disodium sulfite oxidizes to disodium sulfate by the way of hydrolysis emitting two charged hydrogen. Because the process of oxidation-reduction evolves in blood serum the presence of disodium sulfite diminishes the needed presence of aminomercaptopropionic acid or sodium salt for several times as pharmacologically needed to produce and emit charged hydrogen for biologic synthesis, whereas the charged aminothiopropionic radical is permanently and succeedingly incorporated in nucleoproteides of bacteria and viruses and/or in killing parasites until complete exhaustion and consummation. Thus, no toxic action can be incurred, while disodium sulfate the only unassimilable product is eliminated from the organism.

Explaining the possible mechanism of action in controlling bacteria, viruses, and parasites it was observed that all purulent processes of chronic character, suppurations, pustules, furuncles, various abcesses, various eczemas, purulent staphlococcal infections, streptococcal and other bacterial infections, mastites, actinomycosis, actinobacillosis, mycosis, mycetes, endometritis may be healed with therapeutical mixture of this invention. Furthermore, myxovirus infection, mixomatosis and the like infections are successfully controlled. Of the parasitic diseases, the protozoan diseases, parasites of the type ixodides. Teliasis, the parasitic sickness of eye conjunctives in bovine, mange in bovine and all animal are successfully exterminated with therapeutical mixture of this invention.

The application in humans is fulfilled with one injection at intervals of one or two days. The applications are fulfilled by priority intravenous, but may be applied intramuscular. If applied intramuscular then the application is made in two places, i.e., in the left and the right thigh. When applied intramuscular certain irritation may be felt, otherwise no other consequences may appear. The doses may be increased until 12 injection in the course of healing. All is worked slowly. The intervals may be longer, which depends on the case. In cases of internal purulent processes and inflamations with suppurations and inner pustule the application must be gradual because the inner pustule may close and form a scar, which may require an operation.

The standard combination of healing ingredients for human use is 200 mg of dry aminomercaptropropionic sodium salt, and 800 mg of dry disodium sulfite, both dissolved before injection in 10 ccm distilled water per 24 hour period.

The standard combination of healing ingredients for animal use is stronger for big animals and the amount varies depending of the net weight of animal. Thus, for each 50 kg net weight of animal 1 ccm of 100 mg of dry aminomercaptopropionic sodium salt, and 300 mg of dry disodium sulfite, both dissolved before injection in 1 ccm distilled water per 24 hour period.

What is claimed is:

1. A method for treating a human or animal host infected with bacteria and viruses or infested with parasites which comprises: administering to said host a pharmaceutical composition comprising aminomercaptopropionic acid or its sodium salt and disodium sulfite in amount effective to give a reducing action in vivo after injection liberating charged hydrogen and charged aminothiopropionic radical for neutralizing bacteria and viruses and killing parasites.

2. The method of claim 1, where the pharmaceutical composition comprises 100 to 200 mg of dry aminomercaptopropionic acid or its sodium salt and 300 to 800 mg of dry disodium sulfite dissolved in 1 to 10 ccm distilled water, which is injected intravenously or intramuscularly in the host in need of such treatment per 24 hour period.

3. The method of claim 1, for treating said human or animal host infected with bacteria or viruses, or infested with parasites which further comprises;
   (a) treating said human or animal host in need of said treatment with repeated administration by intravenous injection or intramuscular injection in two sites with an antibacterial, antiviral and antiparasite effective amount therefor of a pharmaceutical mixture containing as active ingredients aminomercaptopropionic sodium salt and disodium sulfite;
   (b) the dosage range per 24 hour period of the mixture in adult human patient being about 200 mg of dry aminomercaptopropionic sodium salt, and 800 mg of dry disodium sulfite, both dissolved before injection in 10 ccm distilled water; and
   (c) the dosage range per 24 hour period of the mixture for grown animal being about 1 ccm for each 50 kg net weight of the animal, which mixture contains 100 mg of dry aminomercaptopropionic sodium salt, and 300 mg of dry disodium sulfite, both dissolved before injection in 1 ccm distilled water.

* * * * *